United States Patent
Li et al.

(10) Patent No.: US 7,321,422 B2
(45) Date of Patent: Jan. 22, 2008

(54) SERS-ACTIVE STRUCTURES HAVING NANOSCALE DIMENSIONS

(75) Inventors: Zhiyong Li, Palo Alto, CA (US); Shih-Yuan Wang, Palo Alto, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 409 days.

(21) Appl. No.: 10/942,482

(22) Filed: Sep. 16, 2004

(65) Prior Publication Data

US 2006/0055922 A1    Mar. 16, 2006

(51) Int. Cl.
    *G01J 3/44*    (2006.01)
(52) U.S. Cl. ..................................... 356/301
(58) Field of Classification Search ............... 356/301; 427/304; 436/172; 977/700, 893
    See application file for complete search history.

(56) References Cited

U.S. PATENT DOCUMENTS

| | | | |
|---|---|---|---|
| 4,448,485 A * | 5/1984 | Bergman et al. ............ 359/328 |
| 4,674,878 A | 6/1987 | Vo-Dinh |
| 4,944,985 A | 7/1990 | Alexander et al. |
| 5,017,007 A | 5/1991 | Milne et al. |
| 5,255,067 A | 10/1993 | Carrabba et al. |
| 5,527,712 A | 6/1996 | Sheehy |
| 5,609,907 A | 3/1997 | Natan |
| 5,772,905 A | 6/1998 | Chou |
| 5,814,516 A * | 9/1998 | Vo-Dinh ................... 435/287.2 |
| 5,837,552 A | 11/1998 | Cotton et al. |
| 6,149,868 A | 11/2000 | Natan et al. |
| 6,165,911 A | 12/2000 | Calveley |
| 6,365,059 B1 | 4/2002 | Pechenik |
| 6,406,777 B1 | 6/2002 | Boss et al. |
| 6,432,740 B1 | 8/2002 | Chen |
| 6,623,977 B1 | 9/2003 | Farquharson et al. |
| 6,649,683 B2 | 11/2003 | Bell |
| 6,743,368 B2 | 6/2004 | Lee |
| 2001/0002315 A1 * | 5/2001 | Schultz et al. ............ 436/172 |
| 2002/0142480 A1 | 10/2002 | Natan |
| 2003/0059820 A1 * | 3/2003 | Vo-Dinh .................... 356/301 |
| 2003/0120137 A1 | 6/2003 | Pawluczyk |
| 2003/0132392 A1 | 7/2003 | Kuroda et al. |
| 2003/0231304 A1 | 12/2003 | Chan et al. |
| 2004/0009298 A1 * | 1/2004 | Moran et al. ............... 427/304 |
| 2004/0135997 A1 | 7/2004 | Chan et al. |
| 2004/0157237 A1 | 8/2004 | Malak et al. |
| 2005/0206892 A1 * | 9/2005 | Wang et al. ................ 356/301 |
| 2006/0038990 A1 * | 2/2006 | Habib et al. ............... 356/301 |

OTHER PUBLICATIONS

Drew, Christopher, et al., "Metal Oxide-Coated Polymer Nanofibers," Nano Letters, vol. 3, No. 2, 2003, pp. 143-147.
Emory, Steven R., et al., "Screening and Enrichment of Metal Nanoparticles with Novel Optical Properties," J. Phys. Chem. B, vol. 102, No. 3, 1998, pp. 493-496.

(Continued)

*Primary Examiner*—Gregory J. Toatley, Jr.
*Assistant Examiner*—Kara E Geisel (57) ABSTRACT

SERS-active structures including features having nanoscale dimensions are disclosed, including methods for forming such SERS-active structures and methods for forming a plurality of such SERS-active structures. Methods for performing SERS using SERS-active structures also are disclosed.

32 Claims, 7 Drawing Sheets

OTHER PUBLICATIONS

Green, Mino, et al., "SERS Substrates Fabricated by Island Lithography: The Silver/Pyridine System," J. Phys. Chem. B, vol. 107, No. 47, 2003, pp. 13015-13021.

Kamins, T.J., et al., "Chemically vapor deposited Si nanowires nucleated by self-assembled Ti islands on patterned and unpatterned Si substrates," Physica E 13, 2002, pp. 995-998.

Kneipp, Katrin, et al., "Single Molecule Detection Using Surface-Enhanced Raman Scattering (SERS)," Physical Review Letters, vol. 78, No. 9, Mar. 3, 1997, pp. 1667-1670.

Liu, Fong-Ming, et al., "Efficient SERS substrates made by electroless silver deposition into patterned silicon structures," J. Mater. Chem., 14, 2004, pp. 1526-1532.

Michaels, Amy M., et al., "Surface Enhanced Raman Spectroscopy of Individual Rhodamine 6G Molecules on Large Ag Nanocrystals," J. Am. Chem. Soc., vol. 121, No. 43, 1999, pp. 9932-9939.

Pinto, N.J., et al., "Electroless Deposition of Thin Metallic Films on Polymer Fibers Prepared via Electrospinning," Polymer Preprints, 44(2), 138, 2003, pp. 138-139.

Tao, Andrea, et al., "Langmuir-Blodgett Silver Nanowire Monolayers for Molecular Sensing Using Surface-Enhanced Raman Spectroscopy," Nano Letters, vol. 3, No. 9, 2003, pp. 1229-1233.

International Search Report dated Dec. 17, 2006.

Vo-Dinh, Tuan, "Surface-Enhanced Raman Spectroscopy Using Metallic Nanostructures," Trends in Analytical Chemistry, 1998, pp. 557-582, vol. 17 Nos. 8+9.

Vo-Dinh T—"Surface-Enhanced Raman Spectroscopy Using Metallic Nanostructures"—TRAC, trends In Analytical Chemistry vol. 17 No. 8-9—Aug. 9, 1998—pp. 557-582.

* cited by examiner

SERS-ACTIVE STRUCTURES HAVING NANOSCALE DIMENSIONS

FIELD OF THE INVENTION

The invention relates to surface enhanced Raman spectroscopy (SERS). More particularly, the invention relates to SERS-active structures including features having nanoscale dimensions, methods for forming SERS-active structures, methods for forming a plurality of SERS-active structures, and methods for performing SERS using SERS-active structures.

BACKGROUND OF THE INVENTION

Raman spectroscopy is a well-known technique for performing chemical analysis. In conventional Raman spectroscopy, high intensity monochromatic light provided by a light source, such as a laser, is directed onto an analyte (or sample) that is to be chemically analyzed. A majority of the incident photons are elastically scattered by the analyte molecule. In other words, the scattered photons have the same energy, and thus the same frequency, as the photons that were incident on the analyte. However, a small fraction of the photons (i.e., about 1 in $10^7$ photons) are inelastically scattered by the analyte molecules. These inelastically scattered photons have a different frequency than the incident photons. This inelastic scattering of photons is termed the "Raman effect." The inelastically scattered photons may have frequencies greater than, or, more typically, less than the frequency of the incident photons.

When an incident photon collides with a molecule, energy may be transferred from the photon to the molecule or from the molecule to the photon. When energy is transferred from the photon to the molecule, the scattered photon will emerge from the sample having a lower energy and a corresponding lower frequency. These lower-energy Raman scattered photons are commonly referred to in Raman spectroscopy as the "Stokes radiation." A small fraction of the analyte molecules are already in an energetically excited state. When an incident photon collides with an excited molecule, energy may be transferred from the molecule to the photon, which will emerge from the sample having a higher energy and a corresponding higher frequency. These higher-energy Raman scattered photons are commonly referred to in Raman spectroscopy as the "anti-Stokes radiation."

The Stokes and the anti-Stokes radiation is detected by a detector, such as a photomultiplier or a wavelength-dispersive spectrometer, which coverts the energy of the impinging photons into an electrical signal. The characteristics of the electrical signal are at least partially a function of the energy (or wavelength, frequency, wave number, etc.) of the impinging photons and the number of the impinging photons (intensity). The electrical signal generated by the detector can be used to produce a spectral graph of intensity as a function of frequency for the detected Raman signal (i.e., the Stokes and anti-Stokes radiation). A unique Raman spectrum corresponding to the particular analyte may be obtained by plotting the frequency of the inelastically scattered Raman photons against the intensity thereof. This unique Raman spectrum may be used for many purposes such as identifying an analyte, identifying chemical states or bonding of atoms and molecules in the analyte, and determining physical and chemical properties of the analyte. Raman spectroscopy may be used to analyze a single molecular species or mixtures of different molecular species. Furthermore, Raman spectroscopy may be performed on a number of different types of molecular configurations, such as organic and inorganic molecules in either crystalline or amorphous states.

Molecular Raman scattering of photons is a weak process. As a result, powerful, costly laser sources typically are used to generate high intensity excitation radiation to increase the weak Raman signal for detection. Surface enhanced Raman spectroscopy (SERS) is a technique that allows for generation of a stronger Raman signal from an analyte relative to conventional Raman spectroscopy. In SERS, the analyte molecules are adsorbed onto, or placed adjacent to, an activated metal surface or structure (a "SERS-active structure"). The interactions between the molecules and the surface cause an increase in the strength of the Raman signal. The mechanism of Raman signal enhancement exhibited in SERS is not completely understood. Two main theories of enhancement mechanisms have been presented in the literature: electromagnetic enhancement and chemical (or "first layer") enhancement. (For further discussion of these surface enhancement mechanism theories, see A. M. Michaels, M. Nirmal, & L. E. Brus, "Surface Enhanced Raman Spectroscopy of Individual Rhodamine 6G Molecules on Large Ag Nanocrystals," *J. Am. Chem. Soc.* 121, 9932-39 (1999)).

Several SERS-active structures have been employed in SERS techniques, including activated electrodes in electrolytic cells, activated metal colloid solutions, and activated metal substrates such as a roughened metal surface or metal "islands" formed on a substrate. For example, it has been shown that adsorbing analyte molecules onto or near a specially roughened metal surface made from gold or silver may enhance the Raman scattering intensity by factors of between $10^3$ and $10^6$.

Recently, SERS has been performed employing randomly oriented nanometer scale needles, particles, and wires, as opposed to a simple roughened metallic surface. The intensity of the Raman scattered photons from a molecule adsorbed on such a metal surface may be increased by factors as high $10^{14}$. However, the intensity of the Raman scattered photons could be further increased if there was a method for forming SERS-active structures including nanoscale features having particular sizes, shapes, locations, and orientations. Also, the inability to produce such SERS-active structures is impeding research directed to completely understanding the enhancement mechanisms, and therefore, the ability to optimize the enhancement effect. In addition, SERS-active structures require significant time and money to fabricate. If these problems can be overcome, the performance of nanoscale electronics, optoelectronics, and molecular sensors may be significantly improved.

Accordingly, there is a need for SERS-active structures including nanoscale features having well controlled size, shape, location, and orientation, and a method for their manufacture. In addition, there is a need for a method for producing high quantities of such SERS-active structures at relatively low cost.

BRIEF SUMMARY OF THE INVENTION

The present invention, in a number of embodiments, includes SERS-active structures including features having nanoscale dimensions, methods for forming SERS-active structures, methods for forming a plurality of SERS-active structures, and methods for performing SERS using SERS-active structures.

SERS-active structures are disclosed herein that include a substrate and a plurality of features located at predetermined positions on a surface of the substrate. Each feature of the plurality of features includes a SERS-active material. In addition, each feature of the plurality of features has nanoscale dimensions and is separated from other features by a predetermined distance of between about 1 and about 50 nanometers.

A method for forming a SERS-active structure including an array of features having nanoscale dimensions is disclosed. The method includes: providing a mold; forming an array of protrusions at predetermined locations on a surface of the mold, the protrusions having nanoscale dimensions; providing a substrate, the substrate having a surface; applying a layer of deformable material to the surface of the substrate; pressing the mold against the substrate, the array of protrusions in the surface of the mold forming an array of corresponding recesses in the layer of deformable material; removing at least a portion of the layer of deformable material to expose at least a portion of the underlying substrate; applying a substantially continuous layer of SERS-active material to the substrate, the layer of SERS-active material covering the remaining portion of the layer of deformable material and the exposed portion of the underlying surface of the substrate; and removing the remaining portion of the layer of deformable material and the overlying portion of the SERS-active material.

Also disclosed is a method for performing surface enhanced Raman spectroscopy (SERS). The method includes: providing a SERS-active structure, the SERS-active structure comprising a plurality of features located at predetermined positions on a substrate, each of the plurality of features having nanoscale dimensions and including a SERS-active material; providing an analyte adjacent at least one of the plurality of features of the SERS-active structure; irradiating the at least one feature and the analyte; and detecting the Raman scattered radiation.

A SERS system is disclosed that includes a SERS-active structure that includes a substrate and a plurality of features located at predetermined positions on a surface of the substrate. Each feature of the plurality of features includes a SERS-active material. In addition, each feature of the plurality of features has nanoscale dimensions and is separated from other features by a predetermined distance of between about 1 and about 50 nanometers. The SERS system also includes a light source configured to irradiate light onto the SERS-active structure and a detector configured to receive Raman-scattered light scattered by an analyte located adjacent the SERS-active structure.

The features, advantages, and alternative aspects of the present invention will be apparent to those skilled in the art from a consideration of the following detailed description taken in combination with the accompanying drawings.

BRIEF DESCRIPTION OF THE SEVERAL VIEWS OF THE DRAWINGS

While the specification concludes with claims particularly pointing out and distinctly claiming that which is regarded as the present invention, the advantages of this invention can be more readily ascertained from the following description of the invention when read in conjunction with the accompanying drawings in which:

DETAILED DESCRIPTION OF THE INVENTION

The present invention, in a number of embodiments, includes SERS-active structures including features having nanoscale dimensions, methods for forming SERS-active structures, methods for forming a plurality of SERS-active structures, and methods for performing SERS using SERS-active structures.

The methods disclosed herein allow for the fabrication of SERS-active structures including nanoscale features having well controlled size, shape, location, and orientation, which allows for improved enhancement of the Raman scattered signal intensity relative to previous SERS-active structures.

Figure 1A:
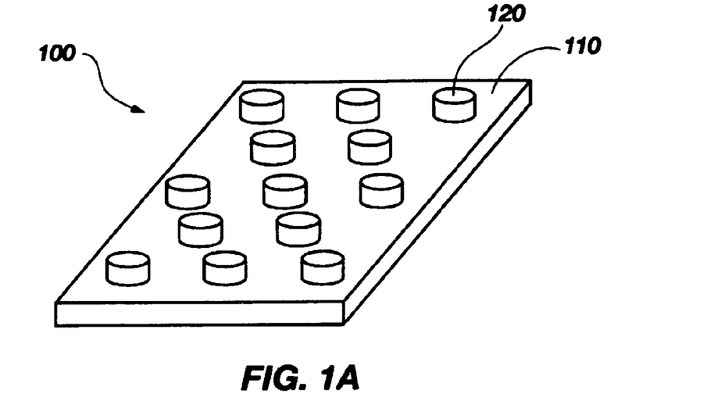
FIG. 1A is a perspective view of a SERS-active structure according to a particular embodiment of the invention.
Figure 1B:
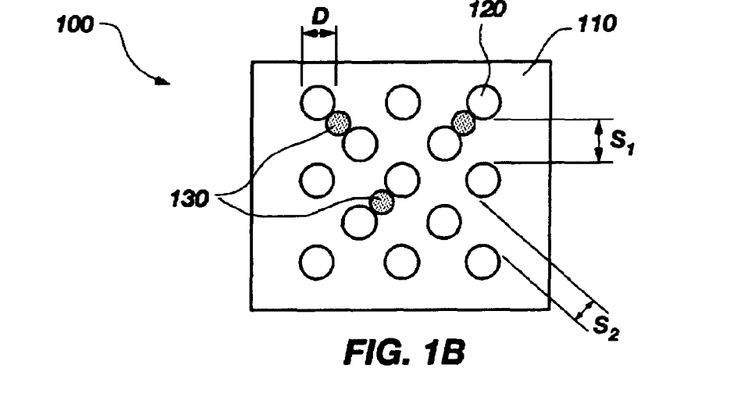
FIG. 1B is a top planar view of the SERS-active structure of FIG. 1A.

An exemplary SERS-active structure 100 is shown in FIGS. 1A-1B that may include a substrate 110 and an array of features 120 disposed at predetermined positions on a surface of the substrate 110. The substrate 110 may be formed from, for example, silicon, other semiconductor materials, ceramics, plastics, metals, or any other suitable material. Each feature 120 may be formed from a SERS-active material such as, for example, gold, silver, copper, platinum, palladium, aluminum, or any other material that will enhance the Raman scattering of photons by analyte molecules positioned adjacent thereto. Analyte molecules 130, illustrated schematically in FIG. 1B, are shown adsorbed adjacent to features 120 on the surface of the substrate 110.

Each feature 120 may include a generally cylindrical column having a diameter D (FIG. 1B) of between about 1 and about 50 nanometers, and a height of between about 1 and about 50 nanometers. In addition some features 120 may have dimensions greater than or less than the dimensions of other features 120. However, the dimensions of each column may be predetermined, selected, and controlled during fabrication. In addition, each feature 120 may be separated from adjacent features 120 by a predetermined spacing of between about 1 and about 50 nanometers. For example, the diameter D shown in FIG. 1B may be about 8 nanometers, the spacing $S_i$ may be about 10 nanometers, and the spacing $S_2$ may be between about 2 and about 5 nanometers.

Figure 2A:
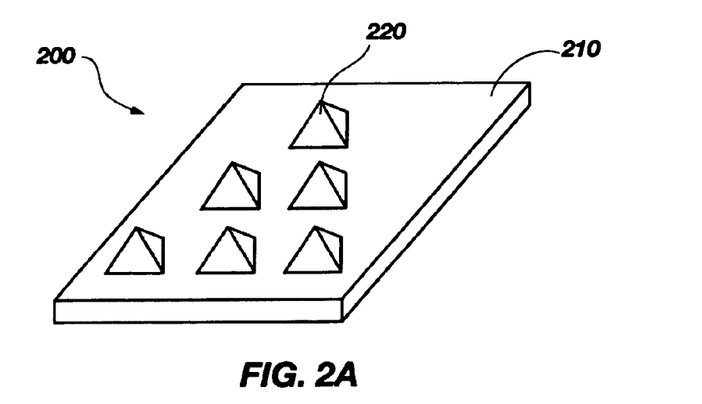
FIG. 2A is a perspective view of a SERS-active structure according to a particular embodiment of the invention.
Figure 2B:
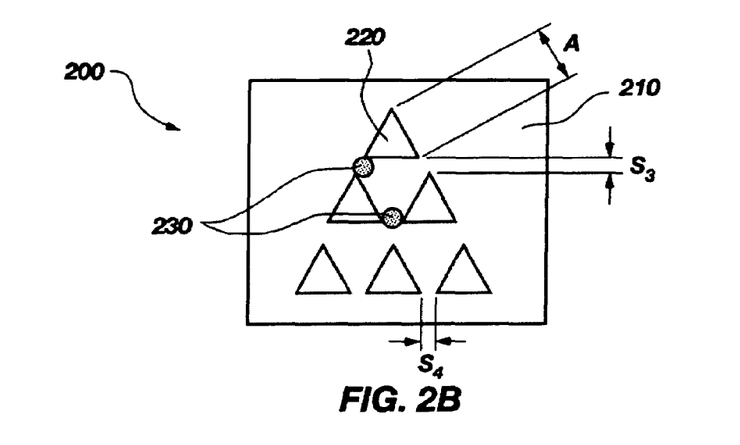
FIG. 2B is a top planar view of the SERS-active structure of FIG. 2A.

An exemplary SERS-active structure 200 is shown in FIGS. 2A-2B, which may include a substrate 210 and an array of features 220 disposed at predetermined positions on a surface of the substrate 210. Analyte molecules 230, illustrated schematically in FIG. 2B, are shown adsorbed adjacent to features 220 on the surface of the substrate 210.

The SERS-active structure 200 may be substantially similar to the SERS-active structure 100 shown in FIG. 1. However, each feature 220 may include a substantially pyramidal structure having a side length A (FIG. 2B) of between about 1 and about 50 nanometers, and a height of between about 1 and about 50 nanometers. For example, the side length A shown in FIG. 2B may be between about 5 and about 15 nanometers, the spacing $S_3$ may be between about 2 and about 10 nanometers, and the spacing $S_4$ may be between about 2 and about 5 nanometers.

Figure 3A:
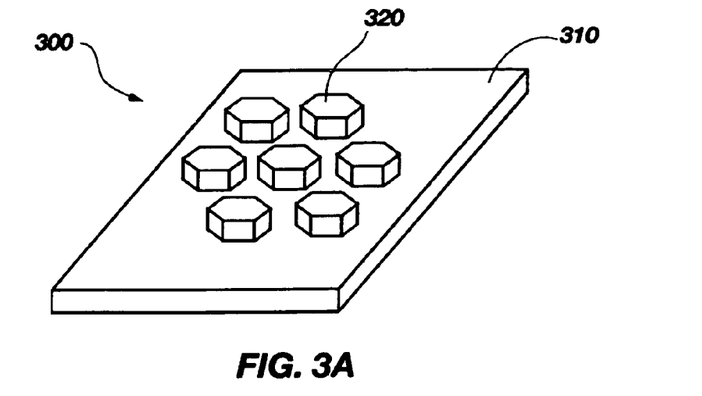
FIG. 3A is a perspective view of a SERS-active structure according to a particular embodiment of the invention.
Figure 3B:
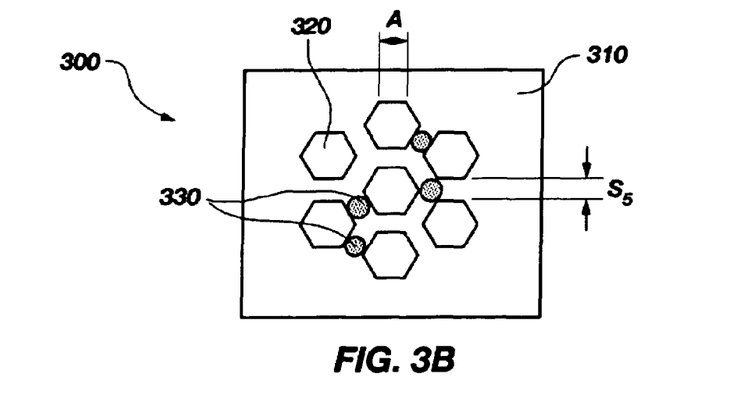
FIG. 3B is a top planar view of the SERS-active structure of FIG. 3A.

An exemplary SERS-active structure 300 is shown in FIGS. 3A-3B that may include a substrate 310 and an array of features 320 disposed at predetermined positions on a surface of the substrate 310. Analyte molecules 330, illustrated schematically in FIG. 3B, are shown adsorbed adjacent to features 320 on the surface of the substrate 310. The SERS-active structure 300 also may be substantially similar to the SERS-active structure 100 of FIG. 1. However, each feature 320 may include a substantially hexagonal column structure having a side length A (FIG. 3B) of between about 1 and about 50 nanometers, and a height of between about 1 and about 50 nanometers. For example, the side length A shown in FIG. 3B may be between about 5 and about 15 nanometers and the spacing $S_5$ may be between about 2 and about 10 nanometers.

Figure 4A:
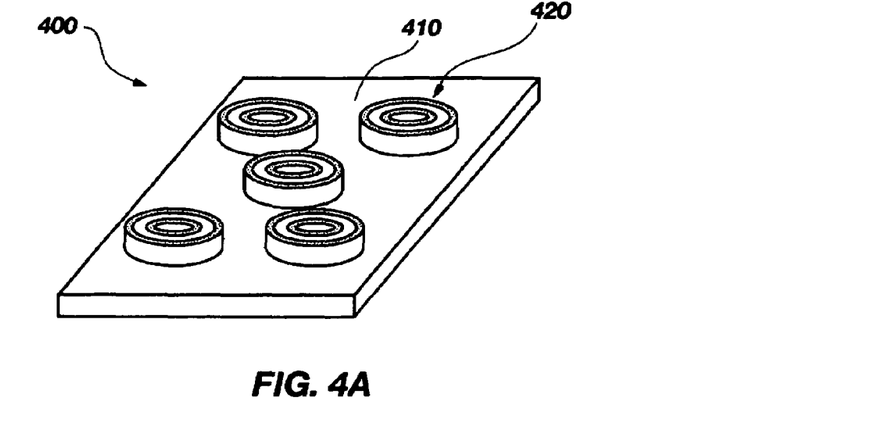
FIG. 4A is a perspective view of a SERS-active structure according to a particular embodiment of the invention.
Figure 4B:
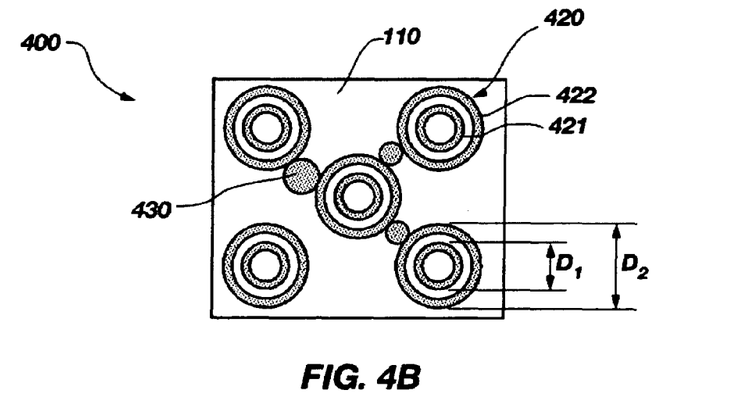
FIG. 4B is a top planar view of the SERS-active structure of FIG. 4A.

An exemplary SERS-active structure 400 is shown in FIGS. 4A-4B that may include a substrate 410 and an array of features 420 disposed at predetermined positions on a surface of the substrate 410. Analyte molecules 430, illustrated schematically in FIG. 4B, are shown adsorbed adjacent to features 420 on the surface of the substrate 410. The SERS-active structure 400 also may be substantially similar to the SERS-active structure 100 of FIGS. 1A-1B. However, each feature 420 may include a hollow inner cylindrical structure 421 and a concentric, hollow outer cylindrical structure 422 (FIG. 4B). Each feature 420 may have a height of between about 1 and about 50 nanometers. The inner cylindrical structure 421 and the outer cylindrical structure 422 may have a diameter of between about 1 and about 50 nanometers. For example, the inner cylindrical structure 421 may have a diameter $D_1$ of between about 10 and about 20 nanaometers and the outer cylindrical structure 422 may have a diameter $D_2$ of between about 20 and about 30 nanaometers. In addition, each feature 420 may be separated from adjacent features 420 by a predetermined spacing of between about 1 and about 50 nanometers, preferably between about 5 and about 15 nanometers.

Figure 5A:
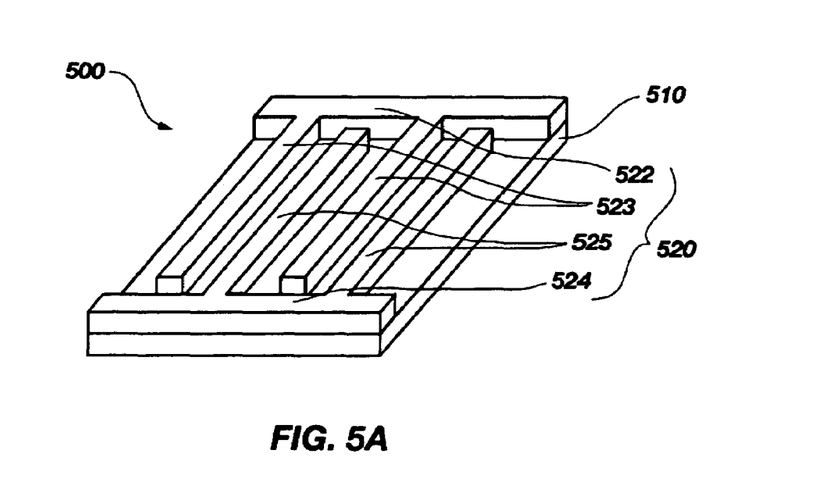
FIG. 5A is a perspective view of a SERS-active structure according to a particular embodiment of the invention.
Figure 5B:
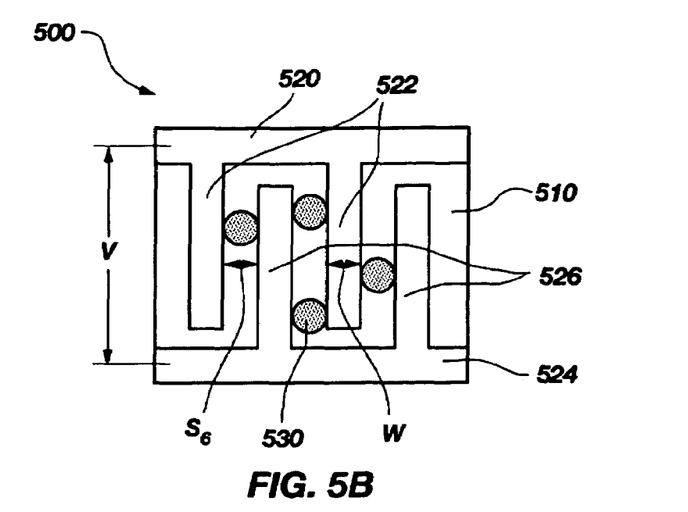
FIG. 5B is a top planar view of the SERS-active structure of FIG. 5A.

Another exemplary SERS-active structure 500 is shown in FIGS. 5A-5B, which may include a substrate 510 and an array of features 520 disposed at predetermined positions on a surface of the substrate 510. The array of features 520 may include a first elongated end bar 522 and a first set of elongated extension bars 523 extending from the end bar 522. The array of features 520 also may include a second elongated end bar 524 and a second set of elongated extension bars 525 extending from the end bar 524. Analyte molecules 530, illustrated schematically in FIG. 5B, are shown adsorbed adjacent to extension bars 522 and extension bars 524 on the surface of the substrate 510. The elongated extension bars 523 may extend between and parallel to the elongated extension bars 525, as shown in FIG. 5B. The extension bars 523, 525 may have a width W of between about 1 and about 50 nanometers, and may be separated laterally from one another by a spacing $S_6$ of between about 1 and about 50 nanometers. For example, the width W shown in FIG. 5B may be between about 5 and about 15 nanometers and $S_6$ may be between about 2 and about 10 nanometers.

In this configuration, a voltage V may be applied between the end bar 522 and the end bar 524 such that an electric potential exists therebetween, thereby generating an electric field between the elongated extension bars 523 and the elongated extension bars 525. By disposing analyte molecules 530 between the elongated extension bars 523 and the elongated extensions bars 525, SERS may be performed while varying the applied voltage V to study the effects of the voltage on the structure of the analyte molecules 530 using the corresponding Raman signal thereof at different voltages. Such a structure may be useful, for example, in the field of molecular electronics.

In each of the SERS-active structures, the size, shape, location, and orientation of the features of the SERS-active structure may be well controlled and may have dimensional tolerances of less than about 5 nanometers, allowing for the production of multiple substantially identical SERS-active structures.

Irradiation of the SERS-active structures 100, 200, 300, 400, 500 with excitation radiation in the visible region of the electromagnetic spectrum may generate strong electromagnetic fields at the surface of the SERS-active structures. The intensity of Raman scattered radiation scattered by an analyte is proportional to the square of the magnitude of any electromagnetic fields experienced by the analyte. Therefore, providing the analyte molecules 130, 230, 330, 430, 530 adjacent the SERS-active structures 100, 200, 300, 400, 500 may enhance the intensity of Raman scattered radiation when the SERS-active structures and the analyte molecules are irradiated with excitation radiation.

Figure 6A:
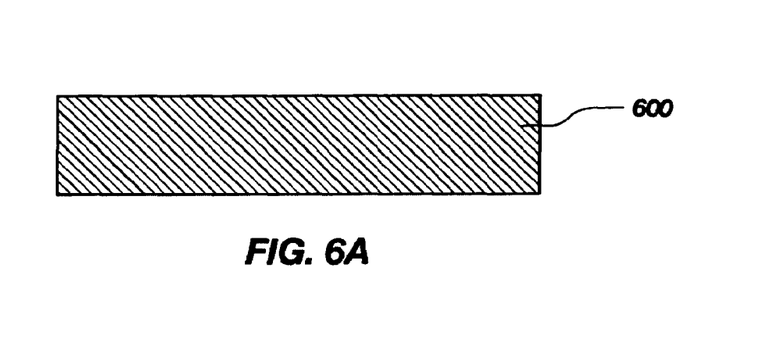
FIGS. 6A-6J illustrate an exemplary method for forming any one of the SERS-active structures of FIGS. 1-5.
Figure 6B:
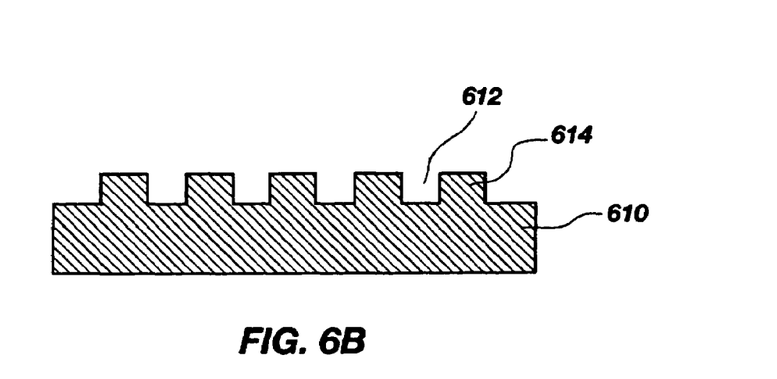

A method for forming any of the exemplary structures 100, 200, 300, 400, and 500 may be described with reference to FIGS. 6A-6J. Referring to FIGS. 6A and 6B, a mold 610 may be formed from a mold substrate 600. The mold substrate 600 may be made from, for example, silicon, other semiconductor materials, ceramics, plastics, metals, or any other suitable material. A series of protrusions 614 and recesses 612 (FIG. 6B) may be formed in a surface of the mold substrate 600 to form the mold 610 using electron beam lithography, reactive ion etching or any other appropriate method known in the art. The size, shape, location, and orientation of the protrusions 614 may be substantially identical to the desired size, shape, location, and orientation of the features 120, 220, 320, 420, 520 of the SERS-active structure (100, 200, 300, 400, 500) to be formed (FIGS. 1-5).

Figure 6C:
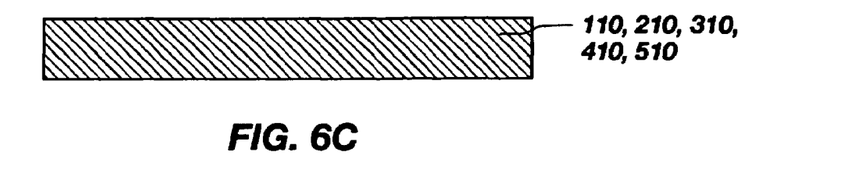
Figure 6D:
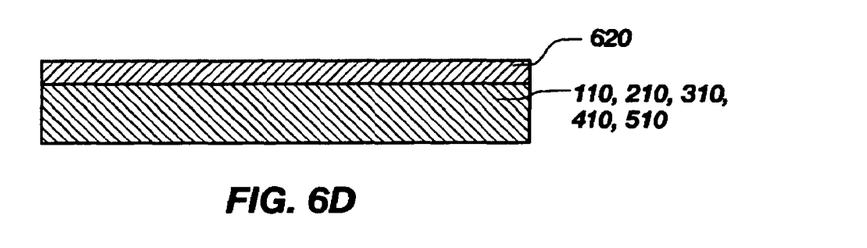

A SERS-active structure substrate such as, for example, substrates 110, 210, 310, 410, 510 may be provided (FIG. 6C), and a layer 620 of deformable material may be applied to a surface thereof (FIG. 6D). The layer 620 of deformable material may include a thermoplastic polymer, such as, for example poly(methyl methacrylate) (PMMA). The thickness of the layer 620 of deformable material may be approximately equal to, or slightly greater than, the height of the features of the SERS-active structure to be formed (i.e., between about 1 and about 50 nanometers). The layer 620 of deformable material alternatively may include many other organic, inorganic, or hybrid materials that will deform under pressure of the mold 610 and that can be further processed as described herein below.

Figure 6E:
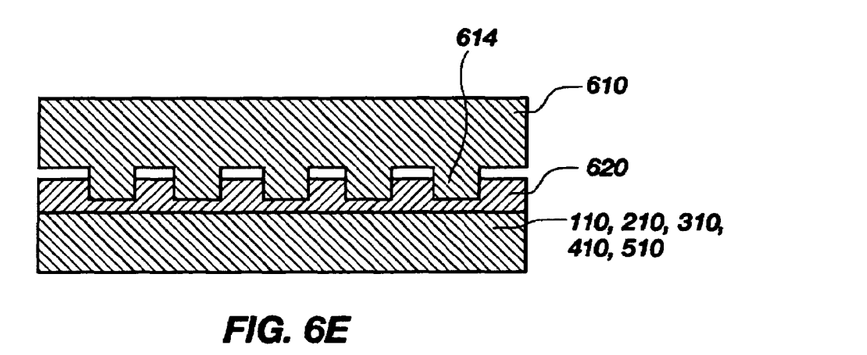
Figure 6F:
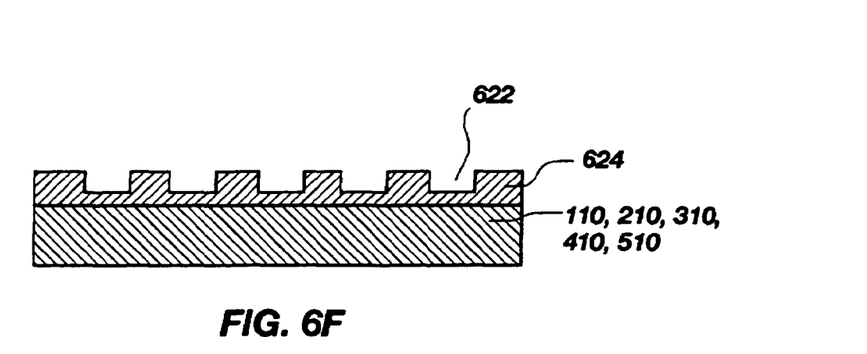

The mold 610 may be pressed against the SERS-active structure substrate 110, 210, 310, 410, 510 such that the protrusions 614 of the mold 610 are pressed into the layer 620 of deformable material, as shown in FIG. 6E. The protrusions 614 and recesses 612 of the mold 610 may form corresponding recesses 622 and protrusions 624 in the layer 620 of deformable material (FIG. 6F). The layer 620 of deformable material may be softened by heating the layer 620 to a temperature above the glass transition temperature of the material prior to pressing the mold 610 against the SERS-active structure substrate. The mold 610 may be removed subsequent to cooling the layer 620 of deformable material to a temperature below the glass transition temperature of the material. Alternatively, the mold 610 may be removed prior to cooling the layer 620 of deformable material if the layer 620 will maintain its shape (i.e., maintain the recesses 622 and protrusions 624) until the temperature of the layer 620 drops below the glass transition temperature of the material.

Figure 6G:
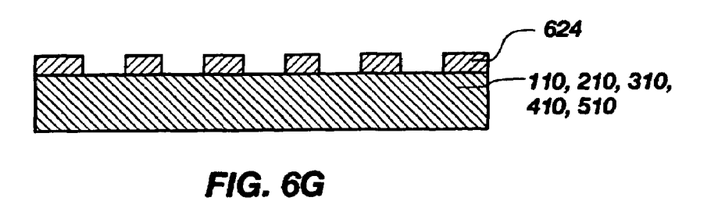

At least a portion of the patterned layer 620 of deformable material may be removed by, for example, reactive ion etching or chemical etching until at least a portion of the underlying SERS-active structure substrate 110, 210, 310, 410, 510 is exposed, as shown in FIG. 6G. Only a portion of the protrusions 624 of the layer 620 of deformable material may remain and the underlying SERS-active structure substrate 110, 210, 310, 410, 510 may be exposed at the regions where the recesses 622 were previously located.

Figure 6H:
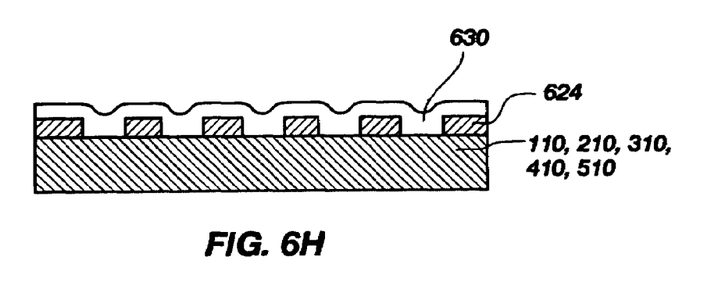
Figure 6I:
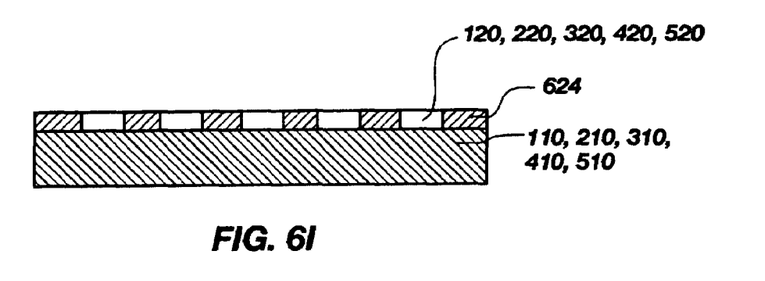

Referring to FIG. 6H, a layer 630 of SERS-active material such as, for example, gold, silver, copper, platinum, palladium, or aluminum, may be applied to the SERS-active structure substrate 110, 210, 310, 410, 510 over the remaining portion of the protrusions 624 of the layer 620 of deformable material. At least a portion of the layer 630 of SERS-active material may then be removed by, for example, chemical-mechanical polishing (CMP) until the protrusions 624 are exposed to provide a substantially smooth, flat surface, as shown in FIG. 6I. The features 120, 220, 320, 420, 520 may be defined by the remaining portion of the layer 630 of SERS-active material between the protrusions 624 of the layer 620 of deformable material.

Figure 6J:
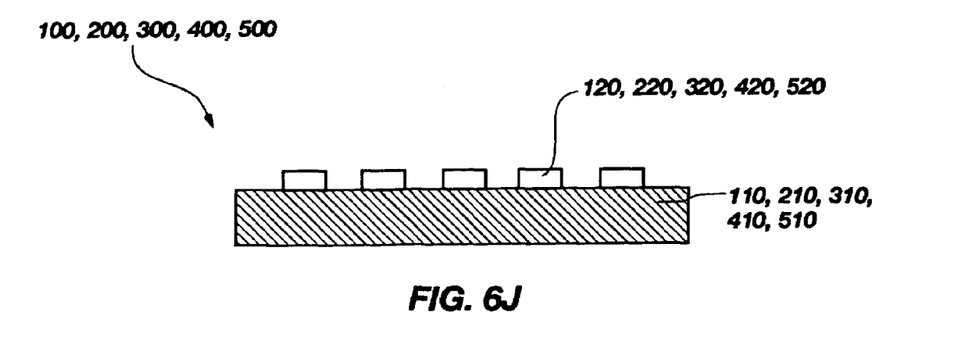

The remaining portions of the protrusions 624 of the layer 620 of deformable material may be removed by, for example, reactive ion etching or chemical etching until only the features 120, 220, 320, 420, 520 remain on the surface of the SERS-active structure substrate 110, 210, 310, 410, 510, thereby forming the SERS-active structure 100, 200, 300, 400, 500 as shown in FIG. 6J. The SERS-active structure 100, 200, 300, 400, 500 then may be used in a SERS system to enhance the Raman signal of an analyte.

Analyte molecules 130, 230, 330, 430, 530 may be provided adjacent to or absorbed onto the surface of the SERS-active structure 100, 200, 300, 400, 500 adjacent the features 120, 220, 320, 420, 520 when the analyte molecules are to be analyzed by Raman spectroscopy to enhance the intensity of Raman scattered radiation scattered by the analyte molecules.

Figure 7:
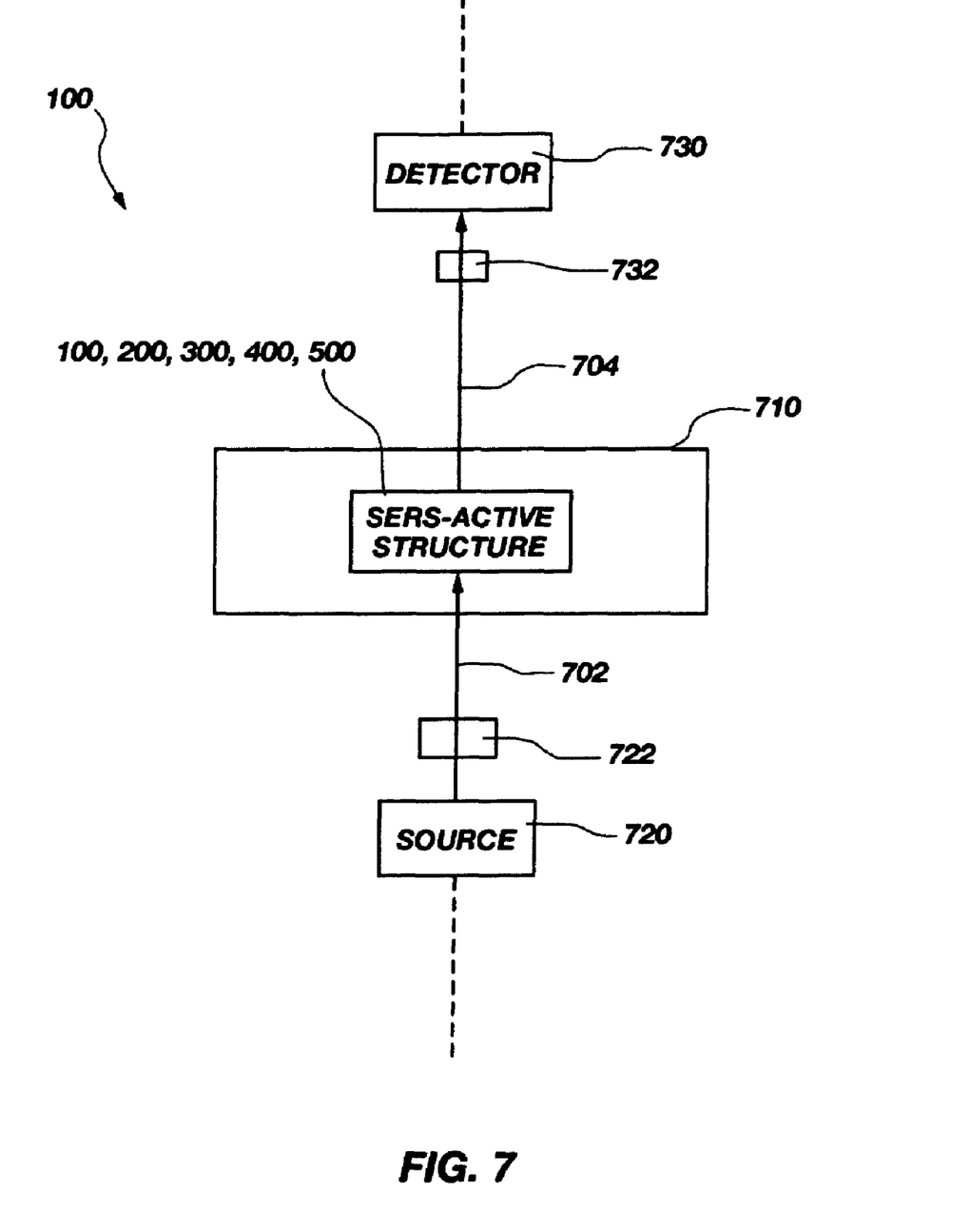
FIG. 7 is a schematic diagram of an exemplary system for performing surface enhanced Raman spectroscopy using any one of the SERS-active structures of FIGS. 1-4.

An exemplary SERS system 700 that may include any of the exemplary SERS-active structures 100, 200, 300, 400, and 500 and may be used to perform surface enhanced Raman spectroscopy is illustrated schematically in FIG. 7. The SERS system 700 may include a sample or analyte stage 710, an excitation radiation source 720, and a detector 730. The analyte stage 710 may include any one of the SERS-active structures 100, 200, 300, 400, and 500 (FIGS. 1, 2, 3, 4, and 5 respectively). The SERS system 700 also may include various optical components 722 positioned between the excitation radiation source 720 and the analyte stage 710, and various optical components 732 positioned between the analyte stage 710 and the detector 730.

The excitation radiation source 720 may be any suitable source for emitting radiation at the desired wavelength and may be capable of emitting a tunable wavelength of radiation. For example, commercially available semiconductor lasers, helium-neon lasers, carbon dioxide lasers, light emitting diodes, incandescent lamps, and many other known radiation emitting sources may be used as the excitation radiation source 720. The wavelengths that are emitted by the excitation radiation source 720 may be any suitable wavelength for properly analyzing the analyte molecules using SERS. An exemplary range of wavelengths that may be emitted by the excitation radiation source 720 includes wavelengths between about 350 nm and about 1000 nm.

The excitation radiation 702 emitted by the source 720 may be delivered either directly from the source 720 to the analyte stage 710 and SERS-active structure 100, 200, 300, 400, 500. Alternatively, collimation, filtration, and subsequent focusing of excitation radiation 702 may be performed by optical components 722 before the excitation radiation 702 impinges on the analyte stage 710 and SERS-active structure 100, 200, 300, 400, 500.

Analyte molecules 130, 230, 330, 430, 530 may be provided adjacent the SERS-active structures 100, 200, 300, 400, 500 to enhance the intensity of Raman scattered radiation when the SERS-active structures and the analyte molecules are irradiated with excitation radiation.

The Raman scattered photons 704 may be collimated, filtered, or focused with optical components 732. For example, a filter or a plurality of filters may be employed, either as part of the structure of the detector 730, or as a separate unit that is configured to filter the wavelength of the excitation radiation 702, thus, allowing only the Raman scattered photons 704 to be received by the detector 730.

The detector 730 receives and detects the Raman scattered photons 704 and may include a monochromator (or any other suitable device for determining the wavelength of the Raman scattered photons 704) and a device such as, for example, a photomultiplier for determining the quantity of Raman scattered photons (intensity).

Ideally, the Raman scattered photons 704 are scattered isotropically, being scattered in all directions relative to the analyte stage 710. Thus, the position of the detector 730 relative to the analyte stage 710 is not particularly important. However, the detector 730 may be positioned at, for example, an angle of 90° relative to the direction of the incident excitation radiation 702 to minimize the intensity of the incident excitation radiation 702 that may be incident on the detector 730.

The methods disclosed herein allow for the reproducible formation of SERS-active structures including nanoscale features having well controlled size, shape, location, and orientation. These structures allow for improved surface-enhanced Raman spectroscopy. The performance of nanoscale electronics, optoelectronics, molecular sensors, and other devices employing the Raman effect may be significantly improved by using the SERS-active structures disclosed herein. In addition, the methods disclosed herein allow for production of high quantities of SERS-active structures at relatively low cost.

Although the foregoing description contains many specifics, these are not to be construed as limiting the scope of the present invention, but merely as providing certain exemplary embodiments. Similarly, other embodiments of the invention may be devised which do not depart from the spirit or scope of the present invention. The scope of the invention is, therefore, indicated and limited only by the appended claims and their legal equivalents, rather than by the foregoing description. All additions, deletions, and modifications to the invention, as disclosed herein, which fall within the meaning and scope of the claims are encompassed by the present invention.

What is claimed is:

1. A SERS-active structure comprising:
   a substrate;
   a plurality of features located at predetermined positions on a surface of the substrate, each feature of the plurality of features including a SERS-active material, each feature of the plurality of features having nanoscale dimensions and being separated from one another by a predetermined distance of between about 1 and about 50 nanometers; and
   an electric potential between at least two features of the plurality of features.

2. The SERS-active structure of claim 1, wherein each feature of the plurality of features is substantially cylindrical having a diameter of between about 1 and about 50 nanometers.

3. The SERS-active structure of claim 2, wherein each feature of the plurality of features has a diameter of between about 5 and about 15 nanometers, each feature of the plurality of features being separated from one another by a predetermined distance of between about 2 and about 10 nanometers.

4. The SERS-active structure of claim 1, wherein each feature of the plurality of features is substantially hexagonal having a side length of between about 1 and about 50 nanometers.

5. The SERS-active structure of claim 4, wherein each feature of the plurality of features has a side length of between about 5 and about 15 nanometers, each feature of the plurality of features being separated from one another by a predetermined distance of between about 2 and about 10 nanometers.

6. The SERS-active structure of claim 1, wherein each feature of the plurality of features is substantially pyramidal having a side length of between about 1 and about 50 nanometers.

7. The SERS-active structure of claim 6, wherein each feature of the plurality of features has a side length of between about 5 and about 15 nanometers, each feature of the plurality of features being separated from one another by a predetermined distance of between about 2 and about 10 nanometers.

8. The SERS-active structure of claim 1, wherein each feature of the plurality of features includes an elongated bar having a thickness of between about 1 nanometer and about 50 nanometers, and having a width of between about 1 and about 50 nanometers.

9. The SERS-active structure of claim 8, wherein each feature of the plurality of features has a width of between about 5 and about 15 nanometers, each feature of the plurality of features being separated from one another by a predetermined distance of between about 2 and about 10 nanometers.

10. The SERS-active structure of claim 1, further comprising an analyte molecule disposed between the at least two features of the plurality of features.

11. The SERS-active structure of claim 1, wherein the dimensions of the plurality of features have a dimensional tolerance of less than about 5 nanometers.

12. A method for forming a SERS-active structure including an array of features having nanoscale dimensions, the method comprising the steps of:
    providing a mold;
    forming an array of protrusions at predetermined locations on a surface of the mold, the protrusions having nanoscale dimensions;
    providing a substrate, the substrate having a surface;
    applying a layer of deformable material to the surface of the substrate;
    pressing the mold against the substrate, the array of protrusions in the surface of the mold forming an array of corresponding recesses in the layer of deformable material;
    removing at least a portion of the layer of deformable material to expose at least a portion of the underlying substrate;
    applying a substantially continuous layer of SERS-active material to the substrate, the layer of SERS-active material covering a remaining portion of the layer of deformable material and the exposed portion of the underlying surface of the substrate; and
    removing the remaining portion of the layer of deformable material and the overlying portion of the SERS-active material.

13. The method of claim 12, wherein the step of forming an array of protrusions comprises forming an array of substantially pyramidal protrusions.

14. The method of claims 12, wherein the step of forming an array of protrusions comprises forming an array of substantially hexagonal protrusions.

15. The method of claim 12, wherein the step of forming an array of protrusions comprises forming an array of substantially cylindrical protrusions.

16. The method of claim 15, wherein each cylindrical protrusion of the array of substantially cylindrical protrusions has a diameter of between about 1 and about 50 nanometers.

17. The method of claim 12, wherein each protrusion of the array of protrusions are separated from one another by a distance of between about 1 and about 50 nanometers.

18. The method of claim 12, wherein the step of providing a mold comprises providing a substrate.

19. The method of claim 18, wherein the substrate is a silicon substrate.

20. The method of claim 18, wherein the step of forming an array of protrusions comprises ion etching.

21. The method of claim 12, wherein the step of applying a layer of deformable material comprises applying a layer of thermoplastic resin.

22. The method of claim 12, wherein the step of applying a substantially continuous layer of SERS-active material comprises applying a substantially continuous layer of one of silver, gold, and copper.

23. The method of claim 12, further comprising the step of chemical mechanical polishing the substantially continuous layer of SERS-active material until at least a portion of the underlying layer of deformable material is exposed therethrough, prior to the step of removing the remaining portion of the layer of deformable material.

24. The method of claim 12, wherein the step of removing the remaining portion of the layer of deformable material and the overlying portion of the SERS-active material comprises etching.

25. The method of claim 12, further comprising the step of heating the layer of deformable material prior to the step of pressing the mold against the substrate.

26. The method of claim 25, further comprising the step of cooling the layer of deformable material subsequent to the step of pressing the mold against the substrate.

27. The method of claim 12, wherein the step of forming an array of protrusions at predetermined locations on a surface of the mold includes forming an array of protrusions having predetermined dimensions for enhancing the Raman scattered signal emitted by an analyte.

28. A method for forming a plurality of SERS-active structures, each of the plurality of SERS-active structures including an array of features having nanoscale dimensions, the method comprising the steps of:
providing a mold;
forming an array of protrusions at predetermined positions in a surface of the mold, the protrusions having nanoscale dimensions;
providing a plurality of substrates, each substrate of the plurality of substrates having a surface;
applying a layer of deformable material to the surface of each substrate of the plurality of substrates;
pressing the mold against each substrate of the plurality of substrates, the array of protrusions in the surface of the mold forming a corresponding array of recesses in the layer of deformable material;
removing at least a portion of the layers of deformable material to expose at least a portion of the underlying surface of each substrate;
applying a substantially continuous layer of SERS-active material to the plurality of substrates, the layer of SERS-active material covering a remaining portions of the layers of deformable material and the exposed portions of the underlying substrates; and
removing the remaining portions of the layers of deformable material and the overlying portions of the SERS-active material.

29. The method of claim 28, wherein the plurality of SERS-active structures are substantially identical.

30. A method for performing surface enhanced Raman spectroscopy (SERS), the method comprising the steps of:
providing a SERS-active structure, the SERS-active structure comprising a plurality of features located at predetermined positions on a substrate, each feature of the plurality of features having nanoscale dimensions, each feature of the plurality of features including a SERS-active material;
providing an analyte adjacent at least one of the plurality of features of the SERS-active structure;
applying a voltage between at least two features of the plurality of features;
irradiating the at least one feature and the analyte; and
detecting the Raman scattered radiation.

31. The method of claim 30, further comprising the steps of:
replacing the SERS-active structure with a second SERS-active structure substantially identical to the first SERS-active structure;
providing an analyte adjacent at least one of the plurality of features of the SERS-active structure;
irradiating the at least one feature and the analyte; and
detecting the Raman scattered radiation.

32. The method of claim 31, wherein applying a voltage between at least two features of the plurality of features comprises applying the voltage subsequent to the step of providing an analyte and prior to the step of irradiating the at least one feature and analyte.

* * * * *

UNITED STATES PATENT AND TRADEMARK OFFICE
CERTIFICATE OF CORRECTION

PATENT NO. : 7,321,422 B2
APPLICATION NO. : 10/942482
DATED : January 22, 2008
INVENTOR(S) : Zhiyong Li et al.

It is certified that error appears in the above-identified patent and that said Letters Patent is hereby corrected as shown below:

In column 4, line 60, delete "Si" and insert -- $S_1$ --, therefor.

In column 7, line 33, delete "FIG. 61." and insert -- FIG. 6I. --, therefor.

In column 10, line 25, in Claim 14, delete "claims 12" and insert -- claim 12 --, therefor.

Signed and Sealed this

Fourteenth Day of July, 2009

JOHN DOLL
*Acting Director of the United States Patent and Trademark Office*